(12) United States Patent
Thompson et al.

(10) Patent No.: US 8,226,295 B2
(45) Date of Patent: Jul. 24, 2012

(54) LASER TARGETING COMPANION SYSTEM USED WITH MEDICAL IMAGING DEVICES

(75) Inventors: Gerald D. Thompson, Turlock, CA (US); Greg K. Thompson, Merced, CA (US); Erin M. Thompson, Turlock, CA (US)

(73) Assignee: Thompson Laser Company, LLC, Merced, CA (US)

( * ) Notice: Subject to any disclaimer, the term of this patent is extended or adjusted under 35 U.S.C. 154(b) by 0 days.

(21) Appl. No.: 12/412,139

(22) Filed: Mar. 26, 2009

(65) Prior Publication Data

US 2010/0246777 A1     Sep. 30, 2010

(51) Int. Cl.
*A61B 6/08*     (2006.01)
*H05G 1/02*     (2006.01)
*G01N 23/083*     (2006.01)

(52) U.S. Cl. ........ 378/206; 378/20; 378/205; 250/491.1
(58) Field of Classification Search ............ 378/20, 378/98.3, 162, 170, 195, 204–206, 210; 250/252.1, 250/491.1; 356/152.2; 315/368.19; 362/553, 362/259, 555, 545, 249.02, 800
See application file for complete search history.

(56) References Cited

U.S. PATENT DOCUMENTS

| | | | |
|---|---|---|---|
| 3,728,027 A | 4/1973 | Watanabe | |
| 3,854,836 A | 12/1974 | Weissman | |
| 4,002,403 A | 1/1977 | Mallozzi et al. | |
| 4,065,211 A | 12/1977 | Vig | |
| 4,078,869 A | 3/1978 | Honeycutt | |
| 4,123,660 A | 10/1978 | Horwitz | |
| 4,132,900 A | 1/1979 | Smith et al. | |
| 4,167,675 A | 9/1979 | Stodberg et al. | |
| 4,223,227 A | 9/1980 | Horwitz | |
| 4,296,329 A | 10/1981 | Mirabella | |
| 4,337,502 A | 6/1982 | Lescrenier | |
| 4,426,726 A | 1/1984 | Cheetham | |
| 4,442,533 A | 4/1984 | Lescrenier | |
| 4,538,289 A * | 8/1985 | Scheibengraber | 378/20 |
| 4,618,980 A | 10/1986 | Lescrenier | |
| 4,625,718 A | 12/1986 | Olerud et al. | |
| 4,659,185 A | 4/1987 | Aughton | |
| 5,031,203 A | 7/1991 | Trecha | |
| 5,212,720 A * | 5/1993 | Landi et al. | 378/206 |
| 5,283,808 A | 2/1994 | Cramer et al. | |
| 5,426,687 A * | 6/1995 | Goodall et al. | 378/206 |
| 5,661,775 A | 8/1997 | Cramer et al. | |
| 5,835,562 A * | 11/1998 | Ramsdell et al. | 378/206 |
| 6,267,502 B1 * | 7/2001 | McNeirney et al. | 378/206 |
| 6,694,169 B2 * | 2/2004 | Kennedy et al. | 600/426 |
| 7,281,849 B2 * | 10/2007 | Sohal et al. | 378/206 |
| 7,794,144 B2 * | 9/2010 | Windt | 378/206 |

* cited by examiner

*Primary Examiner* — Anastasia Midkiff
(74) *Attorney, Agent, or Firm* — Schwegman, Lundberg & Woessner, P.A.

(57) ABSTRACT

In various exemplary embodiments, a targeting device providing a visible indication of an invisible beam is disclosed. The invisible beam, such as an x-ray beam, is emitted by a radiation source on a medical imaging system. The targeting device includes, for example, an illumination source to produce a visible beam and operate at one or more wavelengths. The illumination source, which is opaque to the x-ray beam and would ordinarily cause shadows on the imaging system, is arranged to be mounted outside of a field-of-view of the invisible beam. A beam reflector is mounted next to the illumination source. The beam reflector is fabricated from a material invisible to x-rays and is arranged to be mounted within the field-of-view of the invisible beam. The beam reflector redirects the visible beam produced by the illumination source such that the visible beam is parallel to the field-of-view of the invisible beam.

22 Claims, 4 Drawing Sheets

LASER TARGETING COMPANION SYSTEM USED WITH MEDICAL IMAGING DEVICES

TECHNICAL FIELD

The present application relates generally to the field of medical imaging devices and, in a specific exemplary embodiment, to a targeting device producing a visible beam of light to locate an invisible beam produced by various medical imaging devices.

BACKGROUND

In radiotherapy, for example as practiced in x-ray oncology, a precise amount of radiation, or dose, must be delivered to an accurately and precisely defined portion of a patient's body. However, since high levels of high energy radiation are used during radiation therapy treatment, exposure to the radiation by both medical personnel and the patient should be limited.

Stationary and mobile x-ray examination devices are known which have a C-arm with opposing ends having an x-ray radiation source and a radiation receiver (e.g., an image intensifier), respectively. The C-arm can be readily located so that transirradiation of a patient oriented on a table is possible from a variety of different directions. The table is typically adjustable in three dimensions (i.e., in x-, y-, and z-spatial dimensions).

Radiation treatment plans are designed to maximize radiation delivered to a target while minimizing radiation delivered to healthy tissue. However, even if such a plan is designed, the goals of maximizing target radiation and minimizing healthy tissue radiation may not be achieved if the radiation is not delivered exactly as required by the treatment plan. More specifically, radiation delivery errors as well as poor treatment planning can result in low irradiation of tumors and high irradiation of sensitive healthy tissue. Thus, x-ray examination devices for the transirradiation of a patient must be arranged relative to the patient such that the x-ray source and the radiation receiver lie in the imaging field of the radiation receiver.

However, prior attempts to provide a visible indication of the location of an invisible x-ray beam have been unsuccessful. Such systems are either inaccurate or produce artifacts on imaging screens of the medical devices. The artifacts produced are indicative of hardware used to produce the visible indicators.

SUMMARY

Various embodiments of the inventive subject matter described herein produce a visualization device in the form of one or more visible laser spots. The laser spots are useful in, for example, medical fluoroscopy, to determine an x-ray imaging area on a patient. Embodiments described herein produce the one or more laser spots without leaving unsightly and difficult to interpret artifacts on a resulting image. The artifacts include, for example, lines, circles, or virtually anything else that is not a part of the human body or object being x-rayed.

In an exemplary embodiment, a targeting device providing a visible indication of an invisible beam is described. The invisible beam, such as an x-ray beam, is emitted by a radiation source on a medical imaging system. The targeting device includes, for example, an illumination source to produce a visible beam and operate at one or more wavelengths. The illumination source, which is opaque to the x-ray beam and would ordinarily cause shadows on the imaging system, is arranged to be mounted outside of a field-of-view of the invisible beam. A beam reflector is mounted next to the illumination source. The beam reflector is fabricated from a material invisible to x-rays and is arranged to be mounted within the field-of-view of the invisible beam. The beam reflector redirects the visible beam produced by the illumination source such that the visible beam is parallel to the field-of-view of the invisible beam.

In another exemplary embodiment, an apparatus providing a visible indication of an invisible beam, emitted by a radiation source on a medical imaging system, is described. The apparatus includes, for example, a laser targeting device to produce a visible beam of light and operate at a visible wavelength. The laser targeting device is arranged to be mounted proximate to an image intensifier of the medical imaging system and includes a head block and a laser reflector. The head block is mounted proximate to a peripheral edge of the laser targeting device and outside a field-of-view of the invisible beam. The head block further has at least one laser diode mounted therein. The laser reflector is arranged to mount within the field-of-view of the invisible beam and proximate to the head block. The laser reflector is substantially transparent to the invisible beam and redirects the visible beam of light parallel to the field-of-view of the invisible beam.

In another exemplary embodiment, an apparatus providing a visible indication of an invisible beam, emitted by a radiation source on a medical imaging system, is described. The apparatus includes, for example, a laser targeting device to produce a visible beam of light and operate at a visible wavelength. The laser targeting device includes a head block and a laser reflector. The head block is mounted proximate to a peripheral edge of the laser targeting device and outside a field-of-view of the invisible beam. A laser diode is mounted within the head block. The head block is arranged to provide alignment adjustments to the laser diode in at least two axes. The laser reflector is arranged to mount within the field-of-view of the invisible beam and proximate to the head block. The laser reflector is substantially transparent to the invisible beam and has a reflecting surface in a central portion of the laser reflector angled at approximately 45° relative to the field-of-view of the invisible beam. The reflecting surface redirects the visible beam of light parallel to and in an approximate center position of the field-of-view of the invisible beam.

Each of these exemplary embodiments, and others, is discussed in detail, below.

BRIEF DESCRIPTION OF DRAWINGS

Various ones of the appended drawings merely illustrate exemplary embodiments of the present invention and should not be considered as limiting its scope.

DETAILED DESCRIPTION

The description that follows includes illustrative structures, methods, materials, and techniques that embody the present disclosure. In the following description, for purposes of explanation, numerous specific details are set forth to provide an understanding of various embodiments of the inventive subject matter. It will be evident, however, to those skilled in the art that embodiments of the inventive subject matter may be practiced without these specific details. Further, well-known structures, machining practices, and techniques have not been shown in detail.

As used herein, the term "or" may be construed in an inclusive or exclusive sense. Similarly, the term "exemplary" may be construed merely to mean an example of something or an exemplar and not necessarily a preferred means of accomplishing a goal. Additionally, although various exemplary embodiments discussed below focus on various embodiments and types of laser targeting systems, the embodiments are merely given for clarity in disclosure. Thus, any type of laser or other light-based targeting system, is considered as being within a scope of the present disclosure.

Figure 1:
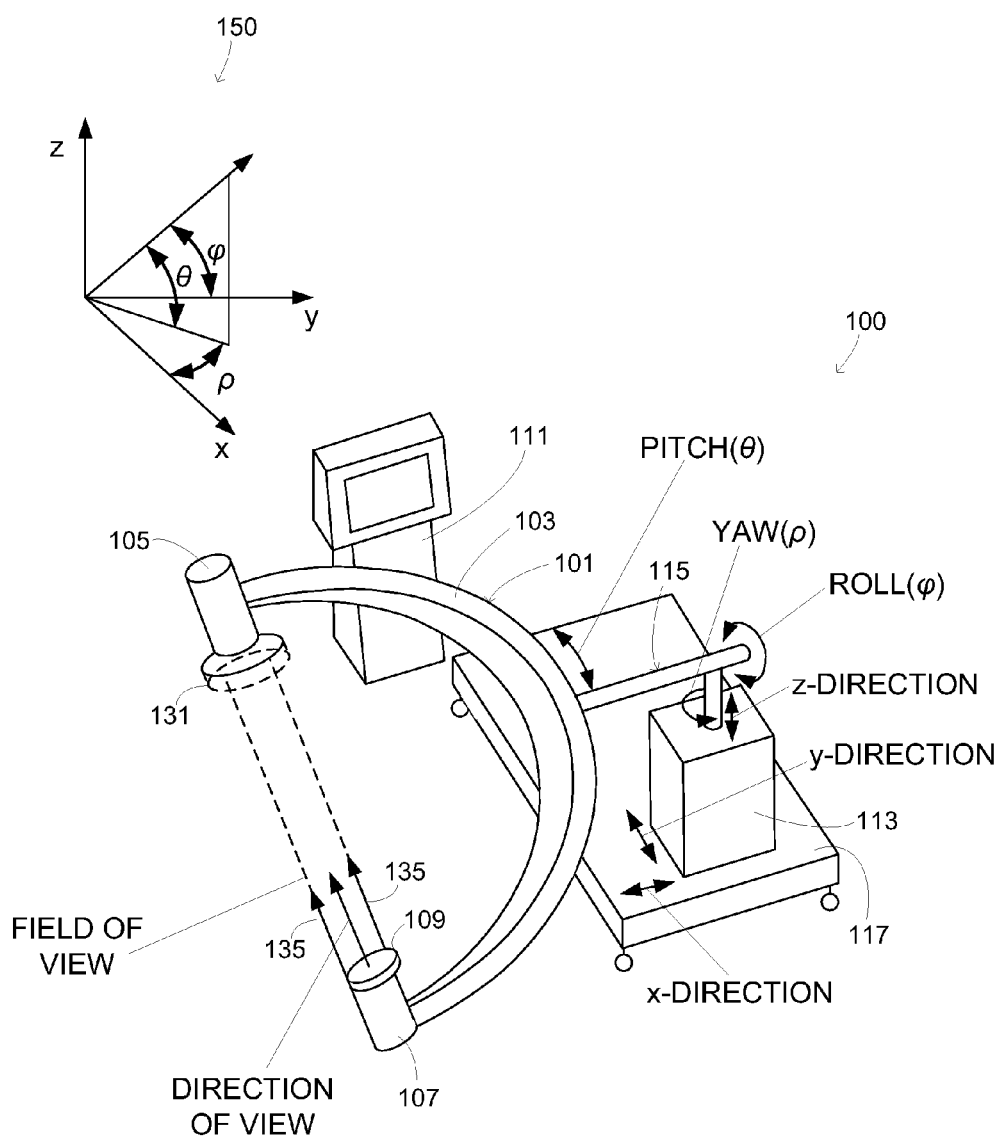
FIG. 1 is a perspective view of a fluoroscopic imaging system with an exemplary laser targeting system mounted thereon.

With reference to FIG. 1, a fluoroscopic imaging system 100 includes a C-arm subsystem 101 for acquiring image information of relevant tissues of a patient (not shown) undergoing examination or surgery. The patient generally would be placed upon a table (not shown but known independently to one skilled in the art) during the imaging process. The C-arm subsystem 101 includes a C-arm 103, an x-ray source 105, and an image intensifier 107. The x-ray source 105 is permanently affixed to a first end of the C-arm 103 such that a direction of view of the image intensifier 107 is always facing toward the x-ray source 105, mounted on an opposing end of the C-arm 103.

Mounted either on or proximate to the image intensifier 107 is a laser targeting device 109. The laser targeting device 109 is arranged between the x-ray source 105 and the image intensifier 107. In another exemplary embodiment (not shown), the laser targeting device may be mounted on or proximate to the x-ray source 105. Details of various exemplary embodiments of the laser targeting device 109 are given in detail, below.

An imaging console 111 allows both control of the C-arm subsystem 101 and image acquisition from the image intensifier 107. One or more monitors (not shown) are arranged to display acquired images to medical personnel as a two-dimensional fluoroscopic image. It can be appreciated that although these elements are illustrated as being mechanically separate from each other, any combination of these elements can be integrated with each other.

The fluoroscopic imaging system 100 further includes a motor/drive unit 113 on which the C-arm subsystem 101 is supported via a pivot assembly 115. The motor/drive unit 113 is mounted on a base unit 117. The motor/drive unit 113 is configured to provide movement of the C-arm 103 as described by, for example, a Cartesian coordinate system 150. In particular, the motor/drive unit 113 can actuate the pivot assembly 115 to pivot the C-arm 103 about three orthogonal axes (e.g., pitch ($\theta$), roll ($\phi$), and yaw ($\rho$)) to allow imaging of the patient from several different angles.

For example, typical fluoroscopic views include anterior-posterior (0° pitch with either 0° or 180° roll), lateral (90° or 270° pitch with 0° roll), and anterior oblique (45° or 135° pitch with 0° roll). Additionally, the motor/drive unit 113 allows rectilinear translation of the C-arm 103 in three-dimensional spatial directions (e.g., in x-, y-, and z-directions). Thus, provided a given angular orientation of the C-arm 103, a desired region of the patient to be imaged can be located within the field of view between the x-ray source 105 and the image intensifier 107. In the illustrated embodiment, the motor/drive unit 113 is coupled to the base unit 117 via a translational assembly (not shown but known independently to one skilled in the art). In this manner, the motor/drive unit 113 can move relative to the base unit 117 to effect rectilinear translation of the C-arm 103 in the x- and y-directions. Further, the motor/drive unit 113 can move the pivot assembly 115 up and down to effect rectilinear translation of the C-arm 103 in the z-direction. Alternatively or in addition to motion effected by the motor/drive unit 113, a patient table (not shown but readily understood and locatable in the x-ray field-of-view), can be rectilinearly translated as well.

A movable table (not shown) cooperatively functions with the C-arm 103 to position various regions of the patient to be imaged between the x-ray source 105 and the image intensifier 107. Thus, the x-ray source 105, under control of the imaging console 111, emits x-rays. The x-rays transmit through the desired tissue region of the patient and the image intensifier 107 converts the tissue modulated x-rays into electrical signals. The electrical signals are thus representative of two-dimensional images of the tissue. The imaging console 111 receives the electrical signals from the image intensifier 107 and displays a two-dimensional fluoroscopic image of the tissue to medical personnel.

The C-arm subsystem 101 has a field-of-view as shown. The direction of view is defined by a size and orientation of an aperture of the C-arm subsystem 101. In this embodiment, an aperture (not shown) of the image intensifier 107 also limits the field-of-view. The imaging console 111 typically operates the C-arm subsystem 101 in either a continuous mode, whereby x-rays are continuously transmitted between the x-ray source 105 and the image intensifier 107 until inactivated by medical personnel. Alternatively, the imaging console 111 can operate in a pulsed mode, whereby x-rays are periodically transmitted between the x-ray source 105 and the image intensifier 107, thereby limiting radiation exposure both to the patient and the medical personnel.

Regardless of the mode of operation, the medical personnel are unable to visually see the x-ray field-of-view without producing x-rays and noting the field-of-view position on the patient by the resulting fluoroscopic image. However, this procedure exposes both the patient and the medical personnel to excessive x-ray radiation.

In a specific exemplary embodiment, the laser targeting device 109 emits a visible beam of light along a center-line of the field-of-view allowing medical personnel to accurately and precisely position the C-arm 103 without exposing either the patient or the medical personnel to excessive radiation. In another specific exemplary embodiment, the laser targeting device 109 emits a plurality of visible beams of light 135 around a periphery of and concentric with the field-of-view thus showing an extent of the field-of-view of the x-ray for various operating conditions (e.g., size of the beam emitted from the x-ray source combined with any limiting apertures). Although various exemplary embodiments below discuss a single visible beam of light, a skilled artisan will recognize how to apply a plurality of beams based on techniques discussed herein. Also, various embodiments of the inventive subject matter discussed herein are useful in many applications, not only in conjunction with the C-arm subsystem 101, but with many radiological systems that would benefit from a coaxial laser-pointing device where no laser-related artifacts on the final image are desired.

The laser targeting device 109 can be used to position the field-of-view of the x-ray in a variety of ways. For example, with the laser targeting device 109 mounted near the image intensifier 107, the laser targeting device 109 emits a visible beam directly on a posterior side of the patient. Alternatively, the C-arm 103 can be rotated 180° (e.g., a 180° φ-roll) thus positioning the visible beam on an anterior side of the patient. As suggested above, the laser targeting device 109 can also be mounted on or proximate to the x-ray source 105 as indicated in an alternative arrangement 131 of the laser targeting device 109. In this embodiment, the visible beam emitted by the laser targeting device 109 can be positioned at nearly at point on the patient. Since the laser targeting device 109, as described below, is invisible to the emitted x-rays, the laser targeting device 109 has no effect on a resulting fluoroscopic image.

Figure 2A:
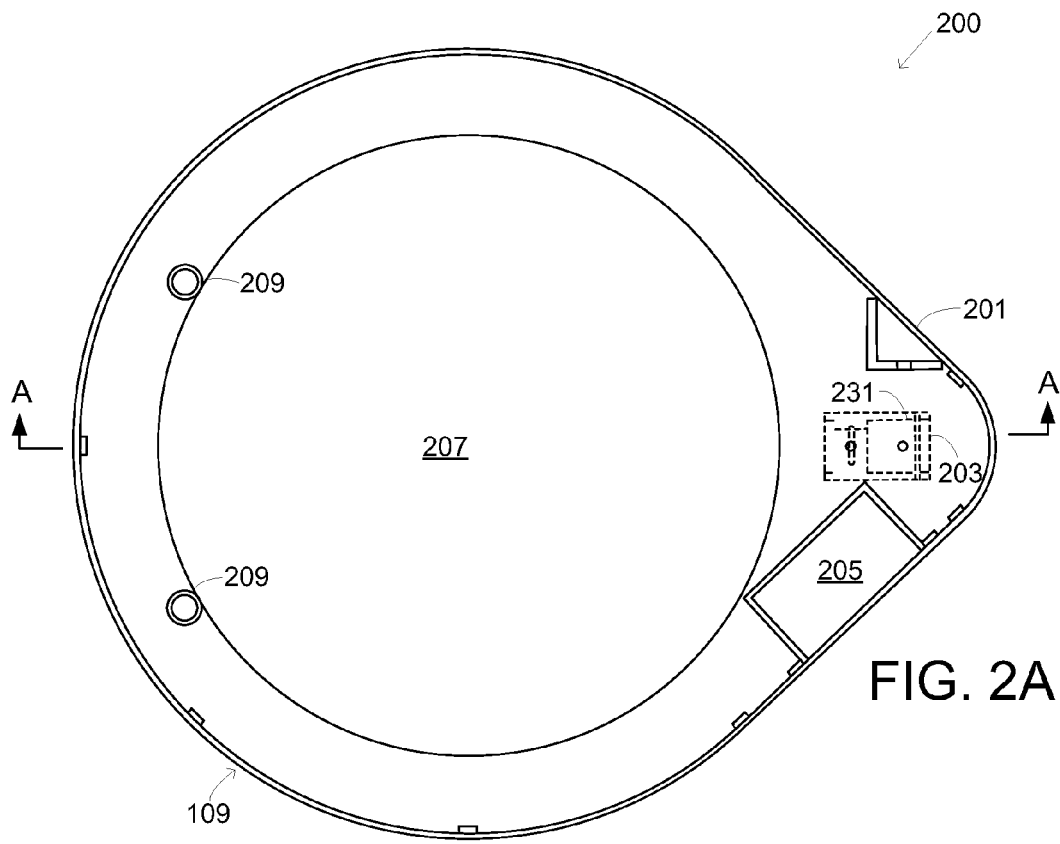
FIG. 2A is a plan view of the exemplary laser targeting system of FIG. 1.

With reference now to FIG. 2A, an exemplary embodiment of a plan view 200 details additional components of the laser targeting device 109. The plan view 200 includes a device sidewall shield 201, a laser fixture module 203, and a battery compartment 205 to provide power for a laser 231 contained within the laser fixture module 203. Details of the laser fixture module 203 are provided, below. The device sidewall shield 201 prevents inadvertent exposure to laser radiation.

A central aperture area 207 is generally kept free of any materials or components that do not transmit x-rays (i.e., any material that may be "visible" to an x-ray imaging system). The central aperture area 207 can be scaled in size as needed for any given field-of-view dimension. For example, the central aperture area 207 can have a diameter of approximately 229 mm (9 inches) or 304 mm (12 inches) to match an external diameter of image intensifiers and x-ray sources found on the market today. Also, a fixed size large enough to fit all image intensifiers and x-ray sources may be fabricated with adapters allowing mounting on any unit. A plurality of mounting posts 209 allow both internal components to be mounted as well as a cover and base plate component, described below.

Figure 2B:
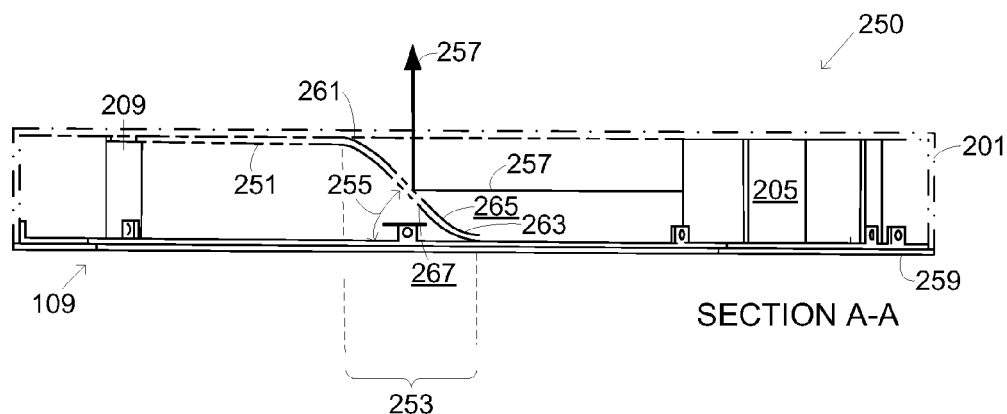
FIG. 2B is a cross-sectional view of an exemplary laser reflector of the laser targeting system of FIG. 1.

Referring now to FIG. 2B, an exemplary cross-sectional view 250 of the laser targeting device 109 includes a laser reflector 251 and a base plate 259. The laser reflector 251 is mounted within the laser targeting device 109 on either the image intensifier 107 or the x-ray source 105. The laser targeting device 109, and consequently, the laser reflector 251 are substantially orthogonal to a field-of-view of the x-ray beam. The laser fixture module 203 (see FIG. 2A) is aligned such that a laser path 257 primarily strikes a first surface 265 of a central portion 253 of the laser reflector 251 and redirects a laser path 257 toward the patient.

In a specific exemplary embodiment, the laser reflector 251 is formed from a sheet of a thermoplastic polymer, such as polycarbonate, polypropylene, polypropene, or any material that is substantially transparent to x-rays. The laser reflector 251 can be relatively thin (e.g., 2.4 mm (0.093 inches) to 2.0 mm (0.080 inches) or less allowing ease in formation and limit any potential absorption of x-ray radiation. Various types of polycarbonates are known in the industry and sold under trade names including Calibre® from Dow Chemical Corporation of Midland Mich., USA, Lexan® from General Electric Company of Schenectady, N.Y., USA, and Makrolon® from Bayer Aktiengesellschaft of Leverkusen, Germany.

Continuing with the specific exemplary embodiment, the central portion 253 of the laser reflector 251 is heated to form an angled area. The laser reflector 251 is fabricated by heating and forming two opposing 50 mm (2 inch) radius curves on the front and rear sides. An angle 255 within the central portion 253 of the laser reflector 251 is 45°. The angle 255 can be formed by heating the laser reflector 251 along an upper 261 and a lower 263 portion of the angle 255.

The first surface 265 of the central portion 253 can be thermally insulated, using techniques known independently in the art, during the heating process to avoid being altered by any potential thermal, mechanical, or chemical reactions of the processing with the laser reflector 251. The insulation can be temporarily applied and avoids possible distortions where the laser path 257 intersects the first surface 265. Whether insulation is useful is a function of the actual material used to form the laser reflector 251.

A skilled artisan will recognize that the angle 255 is not critical as long as, overall, the laser beam emanates from the laser targeting device 109 either parallel to or anti-parallel to the direction of view (see FIG. 1). Parallelism can be achieved in a variety of ways. For example, if either the angle 255 is not 45° or the base plate 259 is not orthogonal to the direction of view, the laser path 257 can be adjusted so that the laser beam as it emanates from the laser targeting device 109 is still parallel to (i.e., the beam diameter is concentric with) the direction of view. Employing a single piece of material for the laser reflector 251 across the entire field of the x-ray field-of-view prevents artifacts in a resulting image.

In alternative exemplary embodiments, the laser reflector 251 can be deposited or otherwise coated with one or more films. The one or more films are chosen such that, when deposited over the laser reflector 251, are still transparent to transmitted x-rays. One skilled in the art in the art will recognize that various films or film stacks can modify various characteristics of the laser reflector 251. For example, an anti-reflective coating (ARC) can be comprised of a single layer of magnesium fluoride ($MgF_2$) or lithium fluoride (LiF). The ARC reduces the air-to-surface reflectance loss from about 4% to less than 1%.

On a second surface 267 in the central portion 253, the laser reflector 251 can be textured in some manner by, for example, sand or bead blasting, glass beading, or sanded with abrasives to break up the reflected surface. The texturing reduces the intensity of or eliminates a second spot from the laser beam being reflected from the second surface of the laser reflector 251 (i.e., a second-surface reflection). Reducing the intensity of or eliminating the second spot assures a single visible output beam. The laser reflector 251 can be mounted with various types of adhesives or mechanical fasteners, all known independently in the art. A side of the laser reflector 251 distal to the laser fixture module 203 (see FIG. 2A) can be fastened mechanically or chemically to the plurality of mounting posts 209.

In another specific exemplary embodiment, the base plate 259 is formed from aluminum. The type of aluminum used is generally unimportant since it is used primarily used for structural considerations. However, an aluminum alloy such as 6061 is suitable (6061 is a precipitation hardened aluminum alloy containing magnesium and silicon). If aluminum is used to form the base plate 259, a central portion, similar in size to the central aperture area 207, is removed allowing x-rays to pass freely therethrough. The base plate 259 may be formed from other materials that transmit x-rays including Vespel®, Celcon®, Delrin®, Teflon®, Arlon® plastics, or other materials such as fluoropolymers, polytetrafluoroethylenes, and polyetheretherketones (PEEK), all known independently in the art. If the material is transmissive at x-ray wavelengths, then the central aperture area 207 can be left intact.

Figure 3:
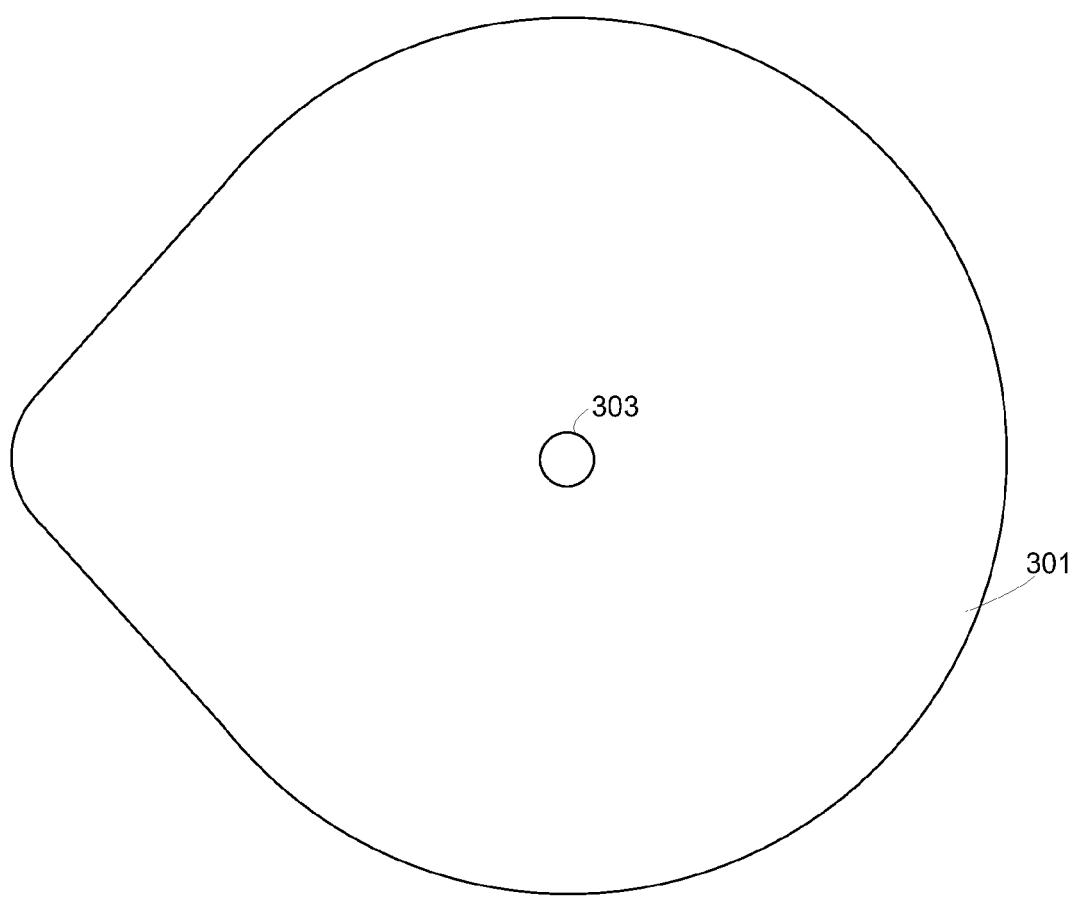
FIG. 3 is an exemplary lid with central aperture for the laser targeting system of FIG. 1.

In FIG. 3, a lid 301 of the laser targeting device 109 (see FIG. 1) includes a central aperture 303. The lid 301 can be formed from a variety of the materials mentioned above. In a specific exemplary embodiment, the lid is formed from polycarbonate sheet material with the central aperture 303 being located as an exit aperture for the laser beam. The lid 301 can be surface textured and painted to leave the central aperture 303 clear. In this exemplary embodiment, the central aperture 303 is approximately 19 mm (0.75 inches) in diameter. However, any size can be used for the central aperture that limits direct human exposure to the beam while not interfering with the beam exiting the laser targeting device 109 is sufficient. In another exemplary embodiment (not shown specifically), the central aperture is physically machined into the lid 301.

Figure 4B:
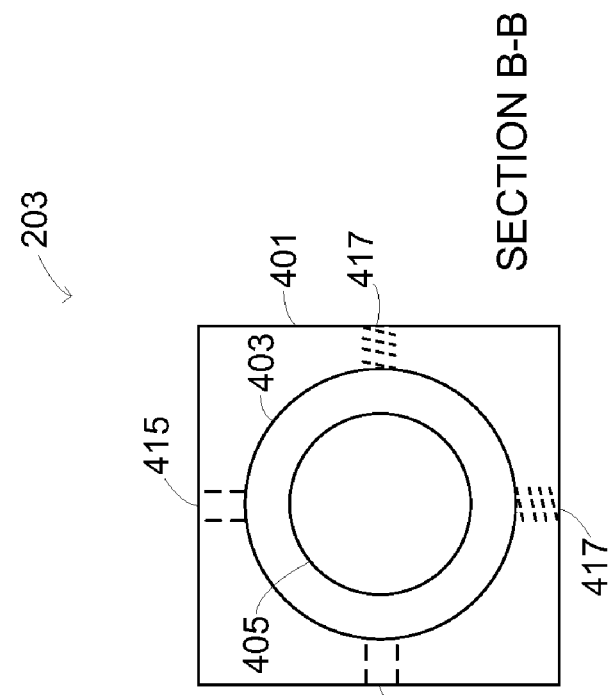
FIG. 4B is a cross-sectional view of the head block of FIG. 4A.
Figure 4A:
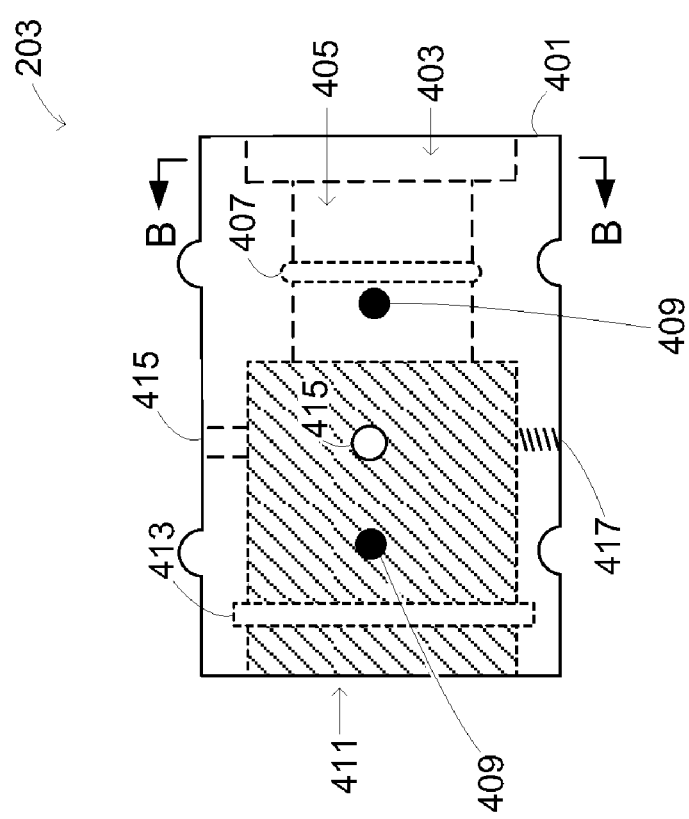
FIG. 4A is a plan view of an exemplary head block used to mount a laser diode in the laser targeting system of FIG. 1.

With reference now concurrently to FIGS. 4A and 4B, an exemplary embodiment of the laser fixture module 203 includes a head-block 401 and provides for mechanical alignment of a laser diode (not shown) with the laser reflector 251 (FIG. 2A). The head-block 401 can be fabricated from a variety of materials since it is located outside the field-of-view of the x-ray (see generally FIGS. 1 and 2A). In a specific exemplary embodiment, the head-block 401 is fabricated from Delrin® (a polyoxymethylene thermoplastic) although other plastics or easily machinable metals such as brass or aluminum can be used as well. The head-block 401 is sized to accommodate a chosen laser, such as a visible laser diode known independently in the art.

A first aperture 403 allows for fine adjustments of the laser diode and any associated optics (not shown). Optical elements are known independently in the art and can include spherical or biconvex lens elements for simple beam focusing (e.g., to produce a minimum spot size on a patient), cylindrical lens elements for producing a line as an output, or apertures or field stops to minimize stray light. Each of these optical elements can be mounted in a small tube (not shown) having external helical threads for mounting into the head-block 401. The uses of optical elements in this way are known independently in the art.

A second aperture 405 forms an outlet path from the laser through the head-block 401. An optional first o-ring groove 407 facilitates mounting of a variety of optical elements, discussed above. A plurality of holes or slots 409 is used to mount the laser fixture module 203 to the base plate 259 (see FIGS. 2A and 2B).

A third aperture 411 accommodates a laser diode (not shown). A second o-ring groove 413 facilitates mechanical alignment of the laser diode. For example, various types of elastomer o-rings (e.g., butadiene, butyl, or silicone rubber) can be sized to provide a press-fit around the laser diode after being fitted within the third aperture 411. Due to the compliant nature of the o-ring, various types of simple alignment mechanisms, described below, such as screw-drives can be fitted around the laser allowing adjustments in both x- and y-directions of the laser diode relative to the central portion 253 of the laser reflector 251.

In a specific exemplary embodiment, the screw-drive mechanism can be a pair of screws 415 mounted orthogonally to one another and tapped into sidewalls of the head-block 401. An optional pair of springs 417 opposes motion of the pair of screws 415 thus fully supporting and maintaining alignment of the laser diode. Alternatively, ball plungers or other spring-based or elastic components may readily be employed as a substitute for the optional pair of springs 417.

In another specific exemplary embodiment, the laser diode is a 2 mW Class III unit, operating at 650 nm. Due to internal losses of the system (front-surface reflection losses, transmission losses, etc.), an output of the laser targeting device may be limited to a Class I or Class II output. In other exemplary embodiments, lasers operating at different wavelengths in the visible range (i.e., generally about 380 nm to 750 nm) and output powers may all be usable. Power leads for the laser diode are passed through the flange and connected to a power switch (not shown) and on to the battery compartment 205 (FIG. 2A).

Although various exemplary embodiments have been described, it will be evident that various modifications and changes may be made to these embodiments without departing from the broader spirit and scope of the invention. Accordingly, the specification and drawings are to be regarded in an illustrative rather than a restrictive sense. The accompanying drawings that form a part hereof show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. For example, the laser targeting device has been defined herein for use with x-ray-based medical systems. However, the targeting device can be used with any source having one or more wavelengths that are normally invisible to the unaided human eye. Further, the targeting device can employ other types of illumination sources other than laser diodes such as light emitting diodes or lasers using a driving current below the lasing threshold. A beam reflector, used with the illumination source, continues to function similarly to the laser reflector described herein. The specification, in general therefore, is not to be taken in a limiting sense, and the scope of various embodiments is defined only by the appended claims, along with the full range of equivalents to which such claims are entitled.

Such embodiments of the inventive subject matter may be referred to herein, individually or collectively, by the term "invention" merely for convenience and without intending to voluntarily limit the scope of this application to any single invention or inventive concept if more than one is, in fact, disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

These and various other embodiments are all within a scope of the present invention. The specification and drawings are, accordingly, to be regarded in an illustrative rather than a restrictive sense.

What is claimed is:

1. A targeting device to provide a visible indication of an invisible beam emitted by a radiation source on a medical imaging system, the targeting device comprising:

an illumination source configured to produce a visible beam and operate at one or more wavelengths, the illumination source being mountable outside of a field-of-view of the invisible beam produced by the radiation source; and a monolithic beam reflector mounted proximate to the beam illumination source and configured to mount within and substantially orthogonal to the field-of-view of the invisible beam, a portion of the monolithic beam reflector being configured to redirect the visible beam produced by the illumination source parallel to the field-of-view of the invisible beam, the monolithic beam reflector assembly being comprised of a single piece of material at least within the field-of-view of the invisible beam to limit artifacts in a resulting image in the medical imaging system, the monolithic beam reflector being transparent to the invisible beam emitted by the radiation source.

2. The targeting device of claim 1, wherein the monolithic beam reflector is arranged to mount over an image intensifier of the medical imaging system.

3. The targeting device of claim 1 wherein the monolithic beam reflector is arranged to mount over the radiation source of the medical imaging system.

4. The targeting device of claim 1, wherein the monolithic beam reflector is comprised of a thermoplastic polymer material.

5. The targeting device of claim 1, wherein the illumination source is a laser diode capable of producing the visible beam and operating at the one or more wavelengths in a range from about 380 nm to 750 nm.

6. The targeting device of claim 1, wherein the illumination source is a light emitting diode capable of producing the visible beam and operating at the one or more wavelengths in a range from about 380 nm to 750 nm.

7. The targeting device of claim 1, wherein the illumination source is arranged to be mounted substantially orthogonal to the field-of-view of the invisible beam, a central portion of the monolithic beam reflector being angled at approximately 45° relative to the field-of-view of the invisible beam.

8. The targeting device of claim 1, further comprising a head block to mount the illumination source, the head block being arranged to provide alignment adjustments to the illumination source in at least two axes.

9. The targeting device of claim 1, wherein the illumination source is arranged to produce the visible beam parallel to and in an approximate center position of the field-of-view of the invisible beam.

10. The targeting device of claim 1, wherein the illumination source is comprised of a plurality of individual visible light sources, the plurality of individual visible light sources being arranged to produce a plurality of the visible beam parallel and approximately on a periphery of the field-of-view of the invisible beam.

11. An apparatus to provide a visible indication of an invisible beam emitted by a radiation source on a medical imaging system, the apparatus comprising:
a laser targeting device configured to produce a visible beam of light and operate at a visible wavelength, the laser targeting device configured to be mounted proximate to an image intensifier of the medical imaging system, the laser targeting device including:
a head block mounted proximate to a peripheral edge of the laser targeting device and outside a field-of-view of the invisible beam, the head block having at least one laser diode mounted therein;
a monolithic laser reflector arranged to mount within the field-of-view of the invisible beam and proximate to the head block, the monolithic laser reflector further configured to redirect the visible beam of light parallel to the field-of-view of the invisible beam, the monolithic laser reflector being comprised of a single piece of material that is transparent to the invisible beam; and
a base plate proximate to the monolithic laser reflector and arranged to be substantially orthogonal to the field-of-view of the invisible beam, the base plate having a central portion similar in size to the field-of-view of the invisible beam emitted by the radiation source, the base plate being formed from a material to allow the invisible beam produced by the radiation source to pass freely therethrough.

12. The apparatus of claim 11, wherein the at least one laser diode operates in a wavelength range from about 380 nm to 750 nm.

13. The apparatus of claim 11, wherein the head block is arranged to be mounted substantially orthogonal to the field-of-view of the invisible beam and a central portion of the monolithic laser reflector is angled at approximately 45° relative to the field-of-view of the invisible beam.

14. The apparatus of claim 11, wherein the head block is arranged to provide alignment adjustments to the at least one laser diode in at least two axes.

15. The apparatus of claim 11, wherein the monolithic laser reflector is comprised of a thermoplastic polymer material.

16. The apparatus of claim 11, wherein the at least one laser diode is arranged to produce the visible beam parallel to and in an approximate center position of the field-of-view of the invisible beam.

17. The apparatus of claim 11, wherein a plurality of the at least one laser diode is arranged to produce a plurality of the visible beam parallel and approximately on a periphery of the field-of-view of the invisible beam.

18. An apparatus to provide a visible indication of an invisible beam emitted by a radiation source on a medical imaging system, the apparatus comprising:
a laser targeting device configured to produce a visible beam of light and operate at a visible wavelength, the laser targeting device including:
a head block mounted proximate to a peripheral edge of the laser targeting device and outside a field-of-view of the invisible beam, the head block having a laser diode mounted therein, the head block being arranged to provide alignment adjustments to the laser diode in at least two axes;
a monolithic laser reflector arranged to mount within the field-of-view of the invisible beam and proximate to the head block, the monolithic laser reflector having a reflecting surface in a central portion of the monolithic laser reflector angled at approximately 45° relative to the field-of-view of the invisible beam and configured to redirect the visible beam of light parallel to and in an approximate center position of the field-of-view of the invisible beam, the monolithic laser reflector being comprised of a single piece of material that is transparent to the invisible beam; and
a base plate proximate to the monolithic laser reflector and arranged to be substantially orthogonal to the field-of-view of the invisible beam, the base plate having a central portion similar in size to the field-of-view of the invisible beam emitted by the radiation source, the base plate being formed from a material to allow the invisible beam produced by the radiation source to pass freely therethrough.

19. The targeting device of claim 18, wherein the laser targeting device is arranged to mount over an image intensifier of the medical imaging system.

20. The targeting device of claim 18, wherein the laser targeting device is arranged to mount over the radiation source of the medical imaging system.

21. The targeting device of claim 1, wherein the monolithic beam reflector is textured on a second surface, the second surface being distal to a first surface arranged to redirect the visible beam.

22. The targeting device of claim 1, further comprising a base plate proximate to the monolithic beam reflector and arranged to be substantially orthogonal to the field-of-view of the invisible beam, the base plate having a central portion similar in size to the field-of-view of the invisible beam produced by the radiation source, the base plate being formed from a material to allow the invisible beam produced by the radiation source to pass freely therethrough.

\* \* \* \* \*